United States Patent [19]

Verkade

[11] Patent Number: 4,626,246
[45] Date of Patent: Dec. 2, 1986

[54] MEDICAL DRAINAGE APPARATUS
[75] Inventor: John G. Verkade, Ames, Iowa
[73] Assignee: Iowa State University Research Foundation, Ames, Iowa
[21] Appl. No.: 542,703
[22] Filed: Oct. 17, 1983
[51] Int. Cl.[4] .............................................. A61M 25/02
[52] U.S. Cl. .................................. 604/174; 128/133; 128/DIG. 26
[58] Field of Search .............................. 604/174–180, 604/280; 128/133, DIG. 26

[56] References Cited

U.S. PATENT DOCUMENTS

| 2,821,194 | 1/1958 | Simmons | 604/180 |
|---|---|---|---|
| 2,831,487 | 4/1958 | Tafilaw | 604/174 |
| 3,194,235 | 7/1965 | Cooke | 128/132 R |
| 3,388,705 | 6/1968 | Grosshandler | 604/283 X |
| 3,722,508 | 3/1973 | Roberts | 604/174 X |
| 3,900,026 | 8/1975 | Wagner | 128/133 |
| 4,018,221 | 4/1977 | Rennie | 128/DIG. 26 |
| 4,353,367 | 10/1982 | Hunter et al. | 604/280 |
| 4,367,735 | 1/1983 | Dali | 128/207.18 |

FOREIGN PATENT DOCUMENTS 666090  7/1963  Canada ............................... 604/284

Primary Examiner—Dalton L. Truluck

[57] ABSTRACT

A medical drainage apparatus is provided for draining surgical wounds or internal organs or cavities. The apparatus comprises a pair of flexible pleated tubes which are adapted to be connected to a pair of drainage tubes which extend from the body, a relatively rigid Y connector which is connected to the flexible tubes, and a relatively rigid bridge which extends over the flexible tubes and which is adapted to be attached to the body and to hold the Y connector.

12 Claims, 3 Drawing Figures

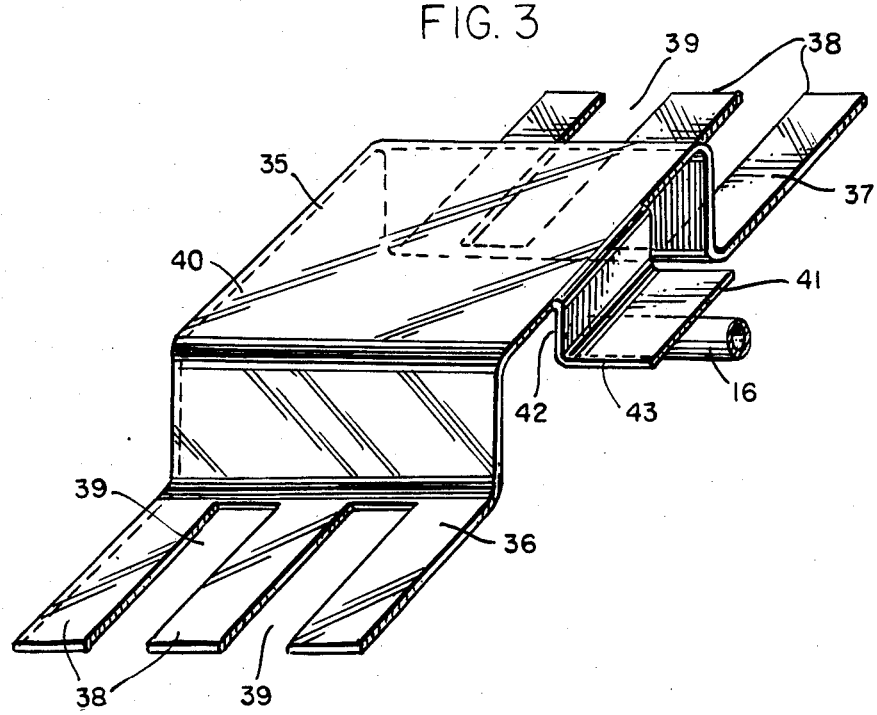

MEDICAL DRAINAGE APPARATUS

BACKGROUND

This invention relates to a medical drainage apparatus, and, more particularly, to a drainage apparatus which does not exert painful forces on the drainage outlet in the body.

Current medical practice commonly provides for drainage of surgical wounds, and the drainage may be assisted by providing a slight vacuum to the drainage tube. Typically, a drainage outlet tube is inserted into the incision, and the vacuum device is connected to the outlet tube by plastic tubing. Although the tubing is flexible, it must be relatively rigid to avoid collapse under the negative pressure provided by the vacuum device and to avoid kinking as the patient moves. Such tubing is commonly made of Tygon. One type of vacuum device is described in U.S. Pat. No. 3,752,158.

A vacuum device may also be used for draining an internal cavity or organ of the body. For example, U.S. Pat. No. 3,752,158 describes draining the bladder through a drainage tube which is inserted through the skin and through the bladder wall.

Any significant forces which are exerted on the outlet tube which extends from the wound or through the skin cause considerable pain to the patient. The tubing which is connected to the outlet tube can be taped to the patient's body in a comfortable position while the patient is immobile. However, since the patient is generally encouraged to become mobile soon after surgery, the tubing then becomes subjected to forces which will cause painful movements of the outlet tube. The pain encountered discourages the patient from engaging in the desired movement.

SUMMARY OF THE INVENTION

The invention utilizes a short length of very flexible, accordion-pleated tubing between the outlet tube and the conventional drainage tubing. The end of the drainage tubing which is connected to the pleated tube is secured to the body by means of a bridge to prevent relative movement, and as the outlet tube moves relative to the end of the drainage tubing during normal body movement, the pleated tube bends, extends, and compresses without exerting significant forces on the outlet tube. The drainage tubing is held by a bridge which extends over the pleated tube and protects the outlet tube and the pleated tube from contact with bed clothes, dressing gowns, etc. The bridge may be secured to the body by adhesive tape, and an intermediate portion of the bridge secures the drainage tubing.

DESCRIPTION OF THE DRAWING

The invention will be explained in conjunction with an illustrative embodiment shown in the accompanying drawing, in which

FIG. 3 is a perspective view of another embodiment of a bridge.

DESCRIPTION OF SPECIFIC EMBODIMENT

Figure 1:
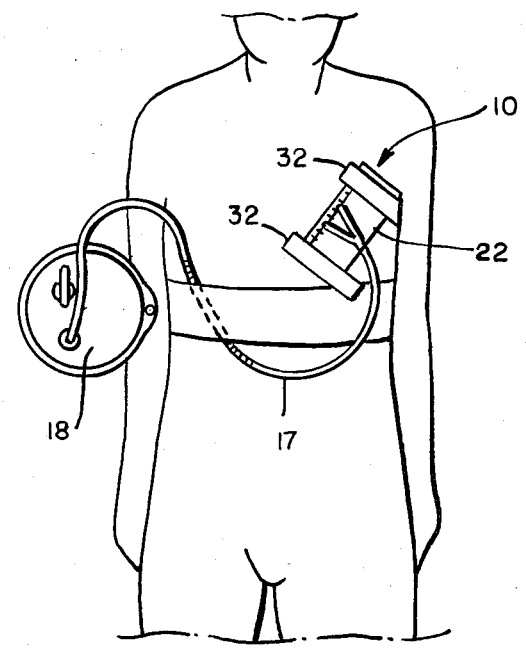
FIG. 1 illustrates a medical drainage apparatus which is formed in accordance with the invention and which is secured to the body of a patient.
Figure 2:
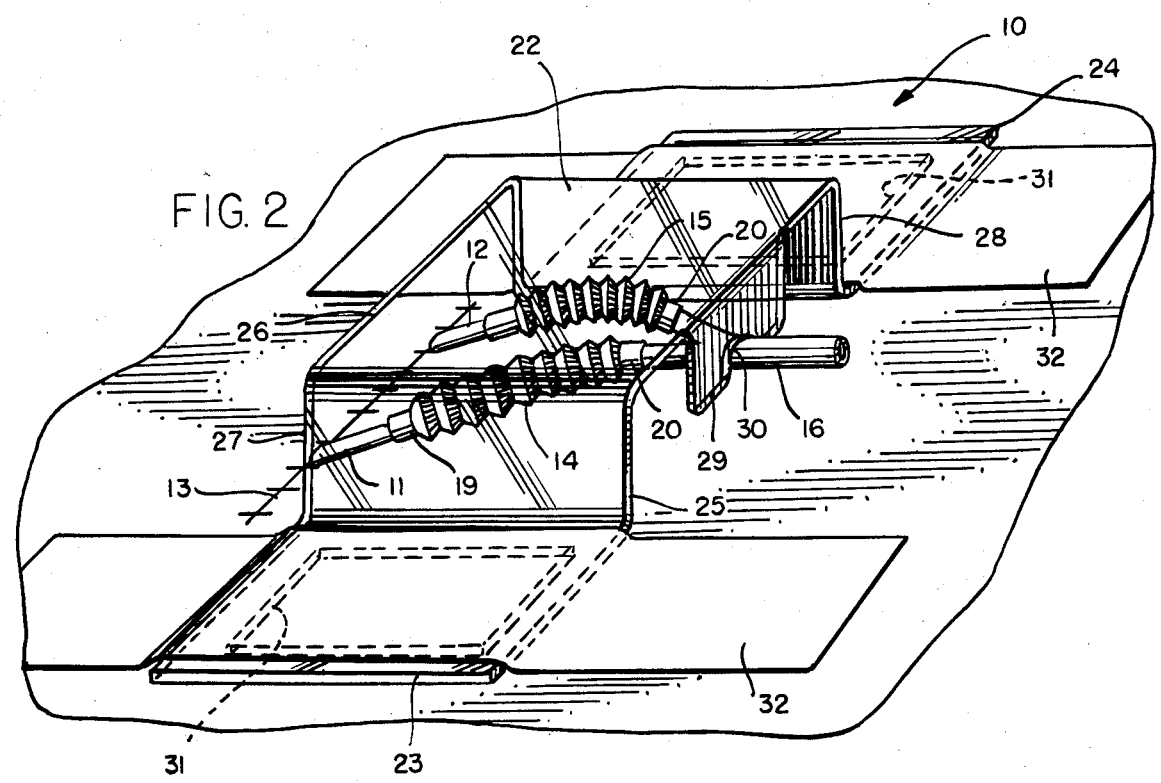
FIG. 2 is an enlarged fragmentary perspective view of the drainage apparatus.

The numeral 10 designates generally a drainage apparatus which is attached to the body of a patient. A pair of outlet tubes 11 and 12 extend from a surgical incision 13 in the patient which has been stitched closed. A pair of flexible accordion-pleated tubes 14 and 15 is connected to the outlet tubes, and the other end of each pleated tube is connected to a Y connector 16. A drainage tube 17 is connected to the middle leg of the Y connector and to a vacuum drainage device 18. Such a drainage device is described in U.S. Pat. No. 3,752,158.

The outlet tubes 11 and 12 are conventional and are formed from relatively rigid medical grade plastic. The drainage tube 17 is also conventional and may be formed, for example, from Tygon plastic. Such tubing, although flexible enough to be bent, is rigid enough so that the tubing does not kink and does not collapse under the negative pressure which is exerted by the drainage device. The Y connector 16 is preferably formed from a more rigid plastic which is relatively inflexible. The outlet tubes 11 and 12, drainage tube 17, and connector 16 are substantially inextensible and will not elongate or compress under the forces which are normally exerted on them.

The accordion-pleated tubes 14 and 15 are also formed from a medical grade plastic. However, the accordion pleats make the tubes 14 and 15 much more flexible than the other tubes and allow the pleated tubes to elongate and compress. Although the pleated tubes are quite flexible, they have enough strength against radial forces to resist collapse under the slight negative pressure which is exerted by the drainage device 18. Accordion-pleated tubes are well-known, and a detailed description of their structure and method of formation is unnecessary herein.

Each of the pleated tubes has a cylindrical end portion 19 which is connected to one of the outlet tubes 11 and 12 and a cylindrical end portion 20 which is connected to one of the legs of the Y connector 16 to form a continuous drainage path between the incision and the drainage device 18. The Y connector can be attached directly to the body of the patient, for example, by adhesive tape, to prevent relative movement of the connector and the body. The flexible pleated tubes 14 and 15 can freely flex, elongate, and compress as the outlet tubes 11 and 12 move relative to the Y connector, and the forces which are exerted on the outlet tubes by the pleated tubes are relatively insignificant and do not cause discomfort to the patient.

The preferred means for holding the Y connector against the body is a bridge 22 which not only holds the connector but covers and protects the outlet tubes and the pleated tubes. The bridge has a pair of flat base portions 23 and 24 and a generally U-shaped central portion 25 which extends between the base portions. The central portion 25 includes a flat intermediate portion 26 which is spaced from the body by guide portions 27 and 28. A tab 29 extends downwardly from one edge of the intermediate portion and is provided with an arcuate recess 30 for rigidly retaining the middle leg of the Y connector.

Each of the base portions 23 and 24 of the bridge is provided with a central opening 31 which exposes most of the skin beneath the base portion. The bridge is attached to the skin of the patient by strips of adhesive tape 32 which extends over each of the base portions. The central opening in each base portion not only permits the skin to breathe but permits the adhesive tape to contact the skin in the central area of the base portion.

The bridge is relatively rigid and is advantageously formed from transparent plastic. The dimensions of the bridge are sufficient to cover the pleated tubes, and the bridge protects the pleated tubes and the outlet tubes from being snagged by bed clothes, dressing gowns, etc. When the bridge is attached to patient, the position of the bridge and the Y connector are adjusted relative to the outlet tubes so that the pleated tubes apply practically zero force on the outlet tubes. After the bridge is secured, relative movement between the outlet tubes and the Y connector during normal body movement can be accommodated by flexing, elongation, and compression of the pleated tubes without exerting forces on the outlet tubes which are sufficient to cause discomfort to the patient.

Another embodiment of a bridge 35 is shown in FIG. 3. The base portions 36 and 37 of the bridge consist of a plurality of laterally extending feet 38 which are separated by spaces 39. The feet can be cut to the desired length by scissors and secured to the body by adhesive tape. The spaces between the feet permit the skin to breathe and permit the adhesive tape to contact the skin between the feet.

The central portion 40 of the bridge 35 includes a generally L-shaped tab 41 which includes a downwardly extending portion 42 and a horizontally extending attaching portion 43 which extends generally parallel to the body. The Y connector 16 can be taped to the attaching portion 43, and the length of the tab portion 42 is such that the Y connector is held away from the body.

Both of the bridges 22 and 35 are advantageously formed of plastic so that unnecessary portions can be cut off to accommodate contours of the patient's body.

In the embodiments illustrated in the drawing, a pair of outlet tubes is connected to a Y connector by a pair of pleated tubes. If desired, however, a single outlet tube can be connected to a single pleated tube and the drainage tube 18 can be connected directly to the pleated tube. The drainage tube can be secured by the bridge in the same way as the Y connector. Furthermore, the drainage apparatus can be used with an outlet tube which drains an internal body cavity or organ rather than a wound or an incision.

While in the foregoing specification a detailed description of specific embodiments of the invention was set forth for the purpose of illustration, it will be understood that many of the details herein given may be varied considerably by those skilled in the art without departing from the spirit and scope of the invention.

I claim:
1. A medical drainage apparatus for draining fluid from the body comprising:
   a tube having a first portion which is adapted to be connected to an area of the body which is to be drained, an intermediate, pleated flexible portion, and a third portion, the pleated flexible portion being able to accommodate relative movement between the first and third portions by flexing, elongation, and compression; and
   a relatively rigid bridge adapted to be secured to the body for holding the third portion of the tube relative to the body, the bridge having a pair of base portions adapted to be attached to the body and an intermediate portion between the base portion which extends over the tube, the intermediate portion of the bridge including a tabe which extend toward the third portion of the tube and holds the third portion.

2. The apparatus of claim 1 in which the tab includes an arcuate recess for engaging the third portion of the tube.

3. The apparatus of claim 1 in which the tab includes an attaching portion which extends generally parallel to the body whereby the third portion of the tube can be taped to the attached portion of the tab.

4. The apparatus of claim 1 in which each of the base portions is generally planar and has a central opening therein, whereby adhesive tape can be applied over each base portion to contact the body through the central opening.

5. The apparatus of claim 1 in which each of the base portions comprises a plurality of laterally extending spaced-apart feet.

6. A medical drainage apparatus for draining fluid from the body comprising:
   a pair of flexible pleated tubes adapted to be connected to an area of the body which is to be drained, the flexible pleated tubes being able to accommodate relative movement between the Y connector and the area of the body which is to be drained by flexing, elongation, and compression;
   a Y connector having a pair of ends connected to the pleated tubes and a third end for delivering fluid which flows through the pleated tubes; and
   a relatively rigid bridge adapted to be secured to the body for holding the Y connector relative to the body, the bridge having a pair of base portions adapted to be attached to the body and an intermediate portion between the base portion which extends over the pleated tubes, an intermediate portion of the bridge including a tab which extends toward the Y connector and holds the Y connector.

7. The apparatus of claim 6 in which the tab includes an arcuate recess for engaging the Y connector.

8. The apparatus of claim 6 in which the tab includes an attaching portion which extends generally parallel to the body whereby the Y connector can be taped to the attaching portion of the tab.

9. The apparatus of claim 6 in which each of the base portions is generally planar and has a central opening therein, whereby adhesive tape can be applied over each base portion to contact the body through the central opening.

10. The apparatus of claim 6 in which each of the base portions comprises a plurality of laterally extending spaced-apart feet.

11. A medical drainage apparatus for draining fluid from the body comprising:
   a pair of flexible pleated tubes adapted to be connected to an area of the body which is to be drained;
   a Y connector having a pair of ends connected to the pleated tubes and a third end for delivering fluid which flows through the pleated tubes, the flexible pleated tubes being able to accommodate relative movement between the y connector and the area of the body which is to be drained by flexing, elongation, and compression; and
   a relatively rigid bridge adapted to be secured to the body for holding the Y connector relative to the body, the bridge having a pair of base portions adapted to be attached to the body and an intermediate portion between the base portion which extends over the pleated tubes, an intermediate portion of the bridge including a tab which extends toward the Y connector and holds the Y connector at end Y connector, said tab including an arcuate recess for engaging the Y connector.

12. A medical drainage apparatus for draining fluid from the body comprising:
 a pair of flexible pleated tubes adapted to be connected to an area of the body which is to be drained;
 a Y connector having a pair of ends connected to the pleated tubes and a third end for delivering fluid which flows through the pleated tubes, the flexible pleated tubes being able to accomodate relative movement between the Y connector and the area of the body which is to be drained by flexing, elongation, and compression; and
 a relatively rigid bridge adapted to be secured to the body for holding the Y connector relative to the body, the bridge having a pair of base portions adapted to be attached to the body and an intermediate portion between the base portion which extends over the pleated tubes, an intermediate portion of the bridge including a tab which extends toward the Y connector and holds the Y connector at end Y connector, said tab including an arcuate recess for engaging the Y connector and an attaching portion which extends generally parallel to the body whereby the second portion of the tube can be taped to the attaching portion of the tab.

* * * * *

UNITED STATES PATENT AND TRADEMARK OFFICE
CERTIFICATE OF CORRECTION

PATENT NO. : 4,626,246

DATED : December 2, 1986

INVENTOR(S) : John G. Verkade

It is certified that error appears in the above-identified patent and that said Letters Patent is hereby corrected as shown below:

Col.3, line 68 change "tabe" to --tab-- and "extend" to --extends--.

Signed and Sealed this

Fourteenth Day of April, 1987

Attest:

DONALD J. QUIGG

*Attesting Officer*  *Commissioner of Patents and Trademarks*